(12) United States Patent
Livoreil

(10) Patent No.: US 7,288,262 B1
(45) Date of Patent: Oct. 30, 2007

(54) COMPOSITION COMPRISING A CYCLOHEXANE-BASED COMPOUND, COMPOUND AND USE OF SAID COMPOUND TO STRUCTURE A COMPOSITION

(75) Inventor: Aude Livoreil, Aulnay sous Bois Cedex (FR)

(73) Assignee: L'Oreal S.A., Paris (FR)

(*) Notice: Subject to any disclaimer, the term of this patent is extended or adjusted under 35 U.S.C. 154(b) by 1223 days.

(21) Appl. No.: 09/666,463

(22) Filed: Sep. 20, 2000

(30) Foreign Application Priority Data

Sep. 21, 1999 (FR) .................................. 99 11773

(51) Int. Cl.
| | |
|---|---|
| A61K 31/21 | (2006.01) |
| A61K 31/16 | (2006.01) |
| A01N 37/18 | (2006.01) |
| C07C 69/74 | (2006.01) |
| C07C 381/00 | (2006.01) |

(52) U.S. Cl. ...................... 424/401; 514/513; 514/599; 514/613; 514/844; 560/1; 560/147; 564/123; 564/151; 564/154; 564/155; 568/75

(58) Field of Classification Search ................ 424/401, 424/70.1, 40.1; 514/513, 599, 613, 844; 560/1, 147; 568/75; 564/123, 151, 154, 564/155
See application file for complete search history.

(56) References Cited

U.S. PATENT DOCUMENTS 3,819,561 A * 6/1974 Bruenner ...................... 260/326
6,372,235 B1 * 4/2002 Livoreil et al. .............. 424/401

FOREIGN PATENT DOCUMENTS

| EP | 0 291 334 | | 11/1988 |
|---|---|---|---|
| EP | 996 029 | * | 4/2000 |
| JP | 03120077 | * | 5/1991 |
| JP | 10212213 | * | 8/1998 |
| JP | 10273477 | * | 10/1998 |
| WO | WO-97/19106 | * | 5/1997 |

OTHER PUBLICATIONS

Fan et al, H-bonding control of molecular aggregation, J. Chem. Soc., Chem. Comm., 1995, vol. 12, pp. 1251-1252.*
Raposo et al, A cyclohexane spacer for phosphate receptors, Tetrahedron Letters, 1995, vol. 36 No. 18, pp. 3255-3258.*
Pryor et al, The activated core approach to combinatorial chemistry: selection of new core molecule, tetrahedron, 1998, vol. 54 No. 6, 4107-24.*
Feng, Collagen-based structures containing the peptoid residue N-isobutyglycine, Biopolymers, 1996, 39 No. 6 pp. 859-72.*
Melacini et al, Collagen-Based Structures containing the Peptoid resicue N-isobutylglycine, J. Am. Chem. Soc., 1996, 118 No. 44, 10725-32.*

Kocis et al, Kemp's triacid scaffolding for synthesis of combinatorial nonpeptide uncoded libraries, tetrahedron Letters, 1995, 36 No. 37, 6623-6.*
Patent Abstracts of Japan, vol. 1998, No. 13, Nov. 30, 1998 (JP 10 212213).
Patent Abstracts of Japan, vol. 1999, No. 01, Jan. 29, 1999 (JP 10 273477).
Patent Abstracts of Japan, vol. 1998, No. 14, Dec. 31, 1998 (JP 10 237034).

* cited by examiner

*Primary Examiner*—Alton Pryor
(74) *Attorney, Agent, or Firm*—Finnegan, Henderson, Farabow, Garrett & Dunner L.L.P.

(57) ABSTRACT

Compositions, in particular cosmetic compositions, comprising a cyclohexane-based compound defined by formula (I):

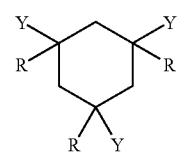

wherein:
R, which may be identical or different, are each chosen from hydrogen atoms and linear and branched, saturated hydrocarbons comprising 1 to 6 carbon atoms;
Y, which may be identical or different, are each chosen from —CO—S—R' groups, —CO—NHR' groups, NH—COR' groups and —S—COR' groups, wherein R', which may be identical or different, are each chosen from
hydrogen atoms,
aryl groups, optionally substituted with at least one hydrocarbon comprising 1 to 22 carbon atoms, wherein said hydrocarbon is chosen from linear and branched, saturated and unsaturated hydrocarbons, and
linear, branched and cyclic, saturated and unsaturated hydrocarbons comprising 1 to 22 carbon atoms, wherein said hydrocarbons may optionally be substituted with at least one group chosen from aryl groups, ester groups, amide groups and urethane groups; wherein said hydrocarbons may optionally comprise at least one hetero atom chosen from O, S and N; and wherein said hydrocarbons may optionally be substituted with at least one entity chosen from fluorine atoms and hydroxyl groups; with the proviso that at least one of said R' comprises at least one unsaturated hydrocarbon. Compounds of formula (I) and their use for structuring a composition, in particular a cosmetic composition.

46 Claims, No Drawings

COMPOSITION COMPRISING A CYCLOHEXANE-BASED COMPOUND, COMPOUND AND USE OF SAID COMPOUND TO STRUCTURE A COMPOSITION

The present invention relates to a composition in particular a solid and also a cosmetic composition, such as a care, treatment and/or make-up composition for the skin, including the scalp and/or for the lips of human beings, said composition comprising a thickened liquid fatty phase and being in particular in the form of a stick or tube of make-up, such as a lipstick.

It is common practice to use a structured, i.e. thickened or gelled, liquid fatty phase in compositions, in particular cosmetic and dermatological compositions, in order to obtain the desired consistency. The thickening of oils (or of phases that are liquid at room temperature) in particular makes it easier to take up the product from its packaging without any significant loss, to limit the diffusion of the product to the local treatment area, to distribute the product uniformly over the local treatment area or to be able to use the product in amounts that are sufficient to obtain the desired cosmetic or dermatological effect. This is especially the case in solid compositions such as deodorants, lip balms and lipsticks, concealer products and cast foundations. This thickening is of prime importance in particular for care, hygiene or make-up compositions such as lipsticks which need to be distributed homogeneously over the local surface to be treated, as well as for hair compositions which need to be spread and distributed uniformly along the keratin fibers and not run down the forehead, the nape of the neck, the face or into the eyes.

To overcome these problems, use is usually made of waxes or fillers. Unfortunately, these waxes and/or fillers have a tendency to make the composition matt and opaque, which is not always desirable, in particular for a lipstick. Specifically, women are always in search of a lipstick in the form of a tube which gives a glossy film; moreover, certain compositions such as lip balms or ointments can be in the form of translucent, or even transparent, sticks.

It is also known practice to thicken oils with polymeric thickeners. Unfortunately, the known thickeners for oils may have to be used in large amounts in order to obtain a gel of high viscosity, for example of greater than 1.3 Pa·s. However, too large an amount of thickener can give the composition inadequate cosmetic properties, in particular a sticky feel and a lack of slipperiness, these drawbacks potentially being very inconvenient, or even unsatisfactory.

Moreover, it is also known practice to gel compositions, in particular cosmetic compositions, using a gelling agent of trialkyl tri(alkylaminocarbonyl)cyclohexane type. These gelling agents make it possible to improve the stability of compositions comprising them. However, once again, the gels obtained may have poor transparency.

The structuring of the liquid fatty phase makes it possible in particular to limit its exudation from solid compositions and, in addition, to limit the migration of this phase into wrinkles and fine lines after it has been deposited on the skin or the lips, which is a particularly desired quality for a lipstick. The reason for this is that a large migration of the liquid fatty phase, charged with dyestuffs, leads to an unaesthetic effect around the lips, which particularly accentuates wrinkles and fine lines. This migration is often mentioned by women as a major defect of conventional lipsticks.

The aim of the present invention is to propose the production of a composition, in particular a cosmetic composition, which can be in solid form, and which can have good translucency, or even transparency.

A subject of the invention is thus a composition, in particular a cosmetic or dermatological composition, which may be in solid form, comprising at least one compound defined by formula (I) below:

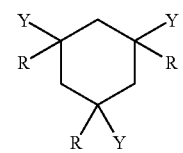

wherein:

R which may be identical or different, are each chosen from hydrogen atoms and linear and branched, saturated hydrocarbons comprising 1 to 6 carbon atoms;

Y, which may be identical or different, are each chosen from —CO—S—R' groups, —CO—NHR' groups, NH—COR' groups and —S—COR' groups, wherein R', which may be identical or different, are each chosen from hydrogen atoms, aryl groups, optionally substituted with at least one hydrocarbon comprising 1 to 22 carbon atoms, wherein said hydrocarbon is chosen from linear and branched, saturated and unsaturated hydrocarbons, and linear, branched and cyclic, saturated and unsaturated hydrocarbons comprising 1 to 22 carbon atoms, wherein said hydrocarbons may optionally be substituted with at least one group chosen from aryl groups, ester groups, amide groups and urethane groups; wherein said hydrocarbons may optionally comprise at least one hetero atom chosen from O, S and N; and wherein said hydrocarbons may optionally be substituted with at least one entity chosen from fluorine atoms and hydroxyl groups; with the proviso that at least one of said R' comprises at least one unsaturated hydrocarbon.

A subject of the invention is also a process for the cosmetic treatment of a support chosen from the skin of the face or of the body, mucous membranes and keratin fibers, comprising the application to said support of a composition as defined above.

Another subject of the invention is the use, in a cosmetic or dermatological composition in solid form and comprising at least one oil, of a sufficient amount of at least one compound of formula (I) to structure/gel said composition.

In particular, the composition can be in the form of a translucent, or even transparent, anhydrous stick. It finds a specific application as an optionally coloured "transfer-resistant" or "non-migrating" composition.

Specifically, it has been found that the use of the compounds of formula (I) makes it possible to greatly structure and thicken liquid (or oily) fatty phases, or even to gel them completely, and thus to obtain stable cosmetic compositions in solid gelled form, which have satisfactory cosmetic properties. These compositions may even be free of waxes while at the same time retaining their rigidity and their good cosmetic properties.

The composition according to the invention can have at least one of the following good cosmetic properties: it is not sticky when applied and is slippery and easy to apply. It produces a homogeneous, uniform film which covers well and is comfortable to wear.

Furthermore, the composition may advantageously be clear, transparent or translucent.

These terms are understood as having their conventional dictionary definitions. Thus, a translucent composition allows light to pass through without, however, allowing the contours of objects to be clearly distinguished. A transparent composition allows light to pass through easily and allows objects to be distinguished clearly through its thickness.

In general, a transparent composition will have a maximum light transmittance value, irrespective of the wavelength, ranging from 400 nm to 800 nm, through a 1 cm thick sample, of at least 35%, such as at least 50% (see EP 291 334, the disclosure of which is incorporated by reference herein).

A translucent composition will have a maximum light transmittance value ranging from 2% to 35%.

The transmittance can be measured by placing a 1 cm thick sample in the light beam of a spectrophotometer working in the wavelengths of the light spectrum.

It has also been found, surprisingly and unexpectedly, that the compositions according to the invention can produce a deposit which may be very shiny and very smooth.

Moreover, the compounds of formula (I) can be used advantageously to prepare "transfer-resistant" compositions, in particular coloured compositions, for which the migration of the coloured film in wrinkles and fine lines, in particular those around the lips or the eyes, is very limited. These compositions can also have the advantage of not being deposited, or of being deposited to only a small extent, on certain supports with which they are placed in contact, such as, for example, a glass, an item of clothing or the skin.

The composition according to the invention thus comprises at least one compound corresponding to formula (I):

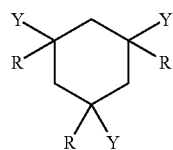

I wherein:

R, which may be identical or different, are each chosen from hydrogen atoms and linear and branched, saturated hydrocarbons comprising 1 to 6 carbon atoms;

Y, which may be identical or different, are each chosen from —CO—S—R' groups, —CO—NHR' groups, NH—COR' groups and —S—COR' groups, wherein R', which may be identical or different, are each chosen from hydrogen atoms, aryl groups, optionally substituted with at least one hydrocarbon comprising 1 to 22 carbon atoms, wherein said hydrocarbon is chosen from linear and branched, saturated and unsaturated hydrocarbons, and linear, branched and cyclic, saturated and unsaturated hydrocarbons comprising 1 to 22 carbon atoms, wherein said hydrocarbons may optionally be substituted with at least one group chosen from aryl groups, ester groups, amide groups and urethane groups; wherein said hydrocarbons may optionally comprise at least one hetero atom chosen from O, S and N; and wherein said hydrocarbons may optionally be substituted with at least one entity chosen from fluorine atoms and hydroxyl groups; with the proviso that at least one of said R' comprises at least one unsaturated hydrocarbon.

The expression "unsaturated hydrocarbon" means a chain which comprises at least one C═C double bond or at least one C≡C triple bond, it being possible, needless to say, for said chain also to be optionally substituted with one or more groups chosen from aryl, ester, amide and urethane groups; and/or optionally to comprise one or more hetero atoms chosen from O, S and N; and/or optionally to be substituted with at least one substituent chosen from fluorine atoms and hydroxyl groups.

At least one of the groups R' thus comprises at least one unsaturated hydrocarbon. This unsaturated hydrocarbon may thus either directly represent said group R', or may be linked to an aryl group; in the latter case, R' thus is an aryl group substituted with said unsaturated hydrocarbon.

It is also possible to have a mixture of these two possibilities.

At least one of the groups R', or at least two groups R', or at least three groups R', can be chosen from linear and branched hydrocarbon comprising only one double unsaturation, comprising 2 to 22 carbon atoms, in particular 10 to 18 carbon atoms, optionally substituted with one or more groups chosen from aryl, ester, amide and urethane groups; and/or optionally comprising one or more hetero atoms chosen from O, S and N; and/or optionally substituted with one or more substituents chosen from fluorine atoms and hydroxyl groups.

The groups R' may be also each chosen from linear and branched hydrocarbons comprising only one double unsaturation, comprising 2 to 22 carbon atoms, in particular 10 to 18 carbon atoms. Non-limiting examples of these hydrocarbons include caproleyl groups, lauroleyl groups, myristoleyl groups, palmitoleyl groups, oleyl groups, gadoleyl groups, linoleyl groups, linolenyl groups and elaidyl groups.

The three groups R' may be identical and may be chosen from the above list.

R may be chosen from a hydrogen atom and a methyl group.

Y may be chosen from —CO—NHR' and —NH—COR'.

In the compound of formula I, the three substitutents represented by Y may be in cis-cis, cis-trans or trans-trans conformation, relative to each other. In particular, at least one of these substituents may be placed in an equatorial position on the cyclohexane ring; all the substituents Y may be placed in an equatorial position.

Representative compounds which may be used in the context of the invention, include the following non-limiting examples:

cis-1,3,5-tris(oleylaminocarbonyl)cyclohexane,
cis-1,3,5-tris(palmitoylaminocarbonyl)cyclohexane,
cis-1,3,5-tris(lauroylaminocarbonyl)cyclohexane,
cis-1,3,5-tris(gadoleylaminocarbonyl)cyclohexane,
cis-1,3,5-tris(elaidylaminocarbonyl)cyclohexane,
cis-1,3-bis(oleylaminocarbonyl)-cis-5-(octadecylaminocarbonyl)cyclohexane,
cis-1,3-bis(oleylaminocarbonyl)-cis-5-(dodecylaminocarbonyl)cyclohexane,
cis-1,3-bis(oleylaminocarbonyl)-cis-5-[N-(3,7-dimethyloctyl)aminocarbonyl]cyclohexane,
cis-1-(oleylaminocarbonyl)-cis-3,5-bis(octadecylaminocarbonyl)cyclohexane,
cis-1-(oleylaminocarbonyl)-cis-3,5-bis(dodecylaminocarbonyl)cyclohexane, cis-1-(oleylaminocarbonyl)-cis-3,5-bis[N-(3,7-dimethyloctyl)aminocarbonyl]cyclohexane,
trans-1,3,5-trimethyl-1,3,5-tris(oleylaminocarbonyl)cyclohexaneand
trans-1,3,5-trimethyl-1,3,5-tris(gadoleylaminocarbonyl)cyclohexane.

The compounds of formula (I) can be prepared according to processes that are well-known to those skilled in the art.

As they are novel, these compounds also form a subject of the invention.

They can be present in the composition in an amount which can readily be determined by a person skilled in the art as a function of the desired effect, and which can generally range from 1% to 40% by weight, for example 2% to 10% by weight, relative to the total weight of the composition, and also 3% to 8% by weight, and further also 4% to 6% by weight.

It has moreover been observed that even the use of a small amount of compounds of formula (I), for example about 2% to 6% by weight, can lead to an adequate gelation of the composition according to the invention. This is due to the high thickening power of the compounds of formula I, which enables them to be effective at low concentration, of about 2% to 6% by weight, whereas it may be necessary to use 10% to 20% by weight of common gelling agents in order to obtain an equivalent result.

Without being bound by the present explanation, it has been observed that the structuring, or gelation, of oils by means of the compounds of formula (I) may be due to the formation of piles in the form of columns of the molecules of compounds of formula (I), resulting in the formation of a network of fibers or lamellae, comprising said compounds of formula (I) and the oils, said network not scattering light, resulting in a certain level of translucency, or even transparency.

The compounds of formula (I) can be used in particular, alone or as a mixture, in a composition which comprises a physiologically acceptable medium, in particular in a cosmetic composition which thus moreover comprises a cosmetically acceptable medium.

The physiologically acceptable medium in which the compounds according to the invention may be used, as well as its constituents, their amounts, the pharmaceutical form of the composition and the method for preparing it, may be chosen by a person skilled in the art on the basis of his general knowledge depending on the type of composition desired.

Generally, but not necessarily, the composition according to the invention comprises at least one cosmetically or dermatologically acceptable oil which is liquid at room temperature (25° C.).

These oils can be hydrocarbon-based oils and/or silicone oils and/or fluoro oils. They can be of animal, plant, mineral or synthetic origin.

Mention may be made of the following non-limiting examples:

hydrocarbon-based oils of animal origin such as perhydrosqualene;

hydrocarbon-based plant oils such as liquid triglycerides of fatty acids of 4 to 10 carbon atoms, such as heptanoic or octanoic acid triglycerides; sunflower oil, corn oil, soybean oil, marrow oil, grapeseed oil, groundnut oil, sweet almond oil, beauty-leaf oil, palm oil, sesame oil, hazelnut oil, apricot oil, macadamia oil, castor oil, avocado oil; caprylic/capric acid triglycerides such as those sold by the company Stearineries Dubois or those sold under the names Miglyol 810, 812 and 818 by the company Dynamit Nobel; jojoba oil, karite butter;

linear and branched hydrocarbons of mineral or synthetic origin, such as liquid paraffins and derivatives thereof, petroleum jelly, polydecenes, purcellin oil and hydrogenated polyisobutene such as parleam;

synthetic esters and ethers, in particular of fatty acids, such as the oils of formula $R_3COOR_4$ in which $R_3$ is chosen from a higher fatty acid residue comprising from 7 to 29 carbon atoms and $R_4$ is chosen from linear and branched hydrocarbon comprising from 3 to 30 carbon atoms, such as, for example, purcellin oil, isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters such as propylene glycol dioctanoate, neopentyl glycol diheptanoate, diethylene glycol diisononanoate; and pentaerythritol esters;

fatty alcohols comprising from 12 to 26 carbon atoms, such as octyldodecanol, 2-butyloctanol, 2-hexyldecanol, 2-undecylpentadecanol and oleyl alcohol;

partially hydrocarbon-based and silicone-containing fluoro oils;

silicone oils chosen from volatile and non-volatile, linear and cyclic polydimethylsiloxanes (PDMSs); alkyldimethicones; silicones modified with aliphatic and/or aromatic groups, which are optionally fluorinated, or with functional groups such as hydroxyl, thiol and/or amine groups; phenylsilicone oils chosen from polyphenylmethylsiloxanes and phenyltrimethicones, mixtures thereof.

The oils used can be volatile and/or non-volatile. The term "volatile oil" means an oil which is capable of evaporating at room temperature from a support onto which it has been applied, in other words an oil which has a measurable vapour pressure at 25° C. and 1 atmosphere, for example greater than 0 Pa, in particular ranging from 10-3 mmHg to 300 mmHg (0.13 Pa to 40,000 Pa).

Mention may be made in particular of volatile silicone oils chosen from volatile cyclic and linear silicones, and cyclocopolymers. Mention may also be made of volatile hydrocarbon-based oils such as isoparaffins and volatile fluoro oils.

The volatile oils may comprise the majority of the oily phase. Thus, they can be present therein in a proportion of at least 50% by weight, including at least 75% by weight, or even 100% by weight, of said oily phase.

The oils can be present in the composition in a proportion generally ranging from 5% to 99% by weight relative to the total weight of the composition, such as from 20% to 75% by weight.

The composition according to the invention can be in solid form. This means that, in the absence of mechanical or thermal stimulation (in particular heating), no collapse of the composition is observed when it is outside the container containing it.

The composition can thus have the conventional viscoelastic behaviour of a composition of solid type.

Moreover, the hardness of the composition according to the invention can be such that the composition is self-supporting and can disintegrate readily to form a satisfactory deposit on the skin and the lips. This hardness can range from 0.04 N to 3 N, such as 0.1 N to 2.5 N, and further such as from 0.5 N to 2 N. This hardness can be measured according to a method of penetration of a probe into said composition and in particular using a texture analyser (for example TA-XT2 from Rheo) equipped with an acrylic cone with an apex angle of 45°. The hardness measurement is carried out at 22° C. at the centre of 5 samples of said composition, according to the method described in the examples.

Thus, advantageously, this composition may comprise little (less than about 5% by weight relative to the total weight of the composition) or even no wax, while at the same time retaining adequate solidity/rigidity/hardness.

The composition may comprise less than 2% by weight, or even less than 0.5% by weight, of wax. The composition can even contain no waxes (i.e. 0%).

For the purposes of the present invention, a wax is a lipophilic fatty compound, which is solid at room temperature (about 25° C.), which undergoes a reversible solid/liquid change of state, which has a melting point of greater than about 40° C. which may be up to 200° C., and which has an anisotropic crystal organization in the solid state.

The waxes generally used in cosmetics and dermatology are, in particular, natural waxes of animal, plant or mineral origin, such as beeswax, montan wax, carnauba wax, candelilla wax, china wax, flax wax, pine wax, cotton wax, ouricury wax, lignite wax, rice bran wax, sugar cane wax, Japan wax and cork fiber wax.

Mention may also be made of paraffin waxes, microcrystalline waxes, lanolin wax, ozokerites, hydrogenated oils with a melting point of greater than about 40° C., such as hydrogenated jojoba oil, polyethylene waxes derived from the polymerization of ethylene, waxes obtained by Fischer-Tropsch synthesis, fatty acid esters and glycerides with a melting point of greater than about 40° C., silicone waxes such as alkyl, alkoxy and/or esters of poly(di)methylsiloxane that are solid at 40° C.

The composition according to the invention can moreover comprise the constituents usually used in the type of application envisaged.

It can comprise one or more organic solvents chosen in particular from:

ketones that are liquid at room temperature, such as methyl ethyl ketone, methyl isobutyl ketone, diisobutyl ketone, isophorone, cyclohexanone and acetone;

alcohols that are liquid at room temperature, such as ethanol, isopropanol, diacetone alcohol, 2-butoxyethanol and cyclohexanol;

glycols that are liquid at room temperature, such as ethylene glycol, propylene glycol and pentylene glycol;

propylene glycol ethers that are liquid at room temperature, such as propylene glycol monomethyl ether, propylene glycol monomethyl ether acetate and dipropylene glycol mono-n-butyl ether;

short-chain esters (comprising from 3 to 8 carbon atoms in total) such as ethyl acetate, methyl acetate, propyl acetate, n-butyl acetate and isopentyl acetate;

ethers that are liquid at room temperature, such as diethyl ether, dimethyl ether and dichlorodiethyl ether;

alkanes that are liquid at room temperature, such as decane, heptane, dodecane and cyclohexane;

cyclic aromatic compounds that are liquid at room temperature, such as toluene and xylene;

aldehydes that are liquid at room temperature, such as benzaldehyde and acetaldehyde.

It is also possible to incorporate a hydrophilic phase into the composition according to the invention, for example an amount of 0% to 10% by weight relative to the total weight of the composition, such as from 1% to 5% by weight, which can comprise hydrophilic active agents and/or hydrophilic gelling agents. It can in particular comprise moisturizers such as glycerol.

The composition may also comprise a dyestuff which can be chosen from the lipophilic dyes, hydrophilic dyes, pigments and nacres usually used in cosmetic or dermatological compositions and mixtures thereof. This dyestuff is generally present in a proportion of from 0.01% to 40% relative to the total weight of the composition, such as from 5% to 25% by weight.

Thus, the composition can comprise a particulate phase, which is generally present in a proportion of 0% to 30% by weight, and can be 0% to 20% by weight, and which can comprise pigments and/or nacres and/or fillers usually used in cosmetic compositions. The term "pigments" should be understood as meaning white or coloured, mineral or organic particles intended to colour and/or opacify the composition. The term "fillers" should be understood as meaning colourless or white, mineral or synthetic, lamellar or non-lamellar particles intended to give body or rigidity to the composition, and/or softness, a matt effect and uniformity to the make-up result. The term "nacres" should be understood as meaning iridescent particles which reflect light.

The pigments can be white or coloured, mineral and/or organic, of micrometric or nanometric size. Mineral pigments which may be mentioned include titanium dioxide, zirconium dioxide or cerium dioxide, as well as zinc oxide, iron oxide or chromium oxide and ferric blue. Organic pigments which may be mentioned include carbon black and barium, strontium, calcium and aluminium lakes.

Among the nacres which may be envisaged, mention may be made of mica coated with titanium oxide, with iron oxide, with natural pigment or with bismuth oxychloride, as well as coloured titanium mica.

The fillers can be mineral or synthetic, and lamellar or non-lamellar. Mention may be made of talc, mica, silica, kaolin, Nylon powder, polyethylene powder, Teflon, starch, titanium mica, natural mother-of-pearl, boron nitride, microspheres such as Expancel (Nobel Industrie), Polytrap (Dow Corning) and silicone resin microbeads (Tospearls from Toshiba, for example).

The composition according to the invention can also comprise any additive usually used in the field under consideration, in particular in cosmetics, such as antioxidants, fragrances, dyes, essential oils, preserving agents, cosmetic active agents, vitamins, essential fatty acids, sphingolipids, self-tanning compounds such as DHA, sunscreens, surfactants, gelling agents, polymers, in particular hydrocarbon-based polymers such as polybutene, polyalkylenes, polyacrylates and silicone polymers or derivatives which are compatible with fatty substances. These additives can be present in the composition in a proportion generally ranging from 0% to 10% by weight.

Needless to say, a person skilled in the art will take care to select this or these optional additional compound(s), and/or the amount thereof, such that the advantageous properties of the composition according to the invention are not, or are not substantially, adversely affected by the addition envisaged.

The compositions according to the invention are intended to be applied to the skin of the face and of the body, to mucous membranes and/or to one or more keratin fibers such as the nails, the eyelashes or the hair.

They can be in any envisageable pharmaceutical form, such as solid or soft oily gels optionally comprising water; solid or gelled oil-in-water, water-in-oil or multiple emulsions; dispersions of oil in water; multiphase systems, including two-phase systems. They can have the appearance of creams, salves, soft pastes, ointments, cast or moulded solids and, for example, sticks.

They can be in particular in the form of sticks or dishes; and for example in the form of transparent anhydrous rigid gels, and also in the form of translucent or transparent anhydrous sticks.

The gelation of the oil is such that a rigid structure in the form of a tube or a stick can be obtained. When they are coloured, these tubes can give, after application, a deposit of homogeneous colour which does not migrate in the wrinkles and fine lines of the skin, in particular those surrounding the lips, but also those around the eyes.

These compositions find an application in particular as body hygiene compositions, for example in the form of deodorant sticks; as hair compositions, for example as styling sticks or make-up sticks for the hair; as make-up compositions for the skin of the face, skin of the body or for mucous membranes, for example as lipsticks, foundations cast as sticks or dishes, face powders, eyeshadows, fixing bases to be applied to conventional lipsticks, concealer sticks, lip glosses, eyeliners, mascaras or temporary tattoo products; as care compositions for the skin or mucous membranes, for example as lipcare balms or lipcare bases, ointments for the body or daily care cream; as anti-sun compositions or self-tanning compositions.

These compositions may be used as transfer-resistant make-up or care compositions, for example as transfer-resistant lipstick or transfer-resistant foundation.

The invention is illustrated in greater detail in the examples which follow. Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result. The percentages are given on a weight basis, unless otherwise indicated.

EXAMPLE 1

Preparation of cis-1,3,5-tris(oleylaminocarbonyl)cyclohexane 2 g of cis-1,3,5-cyclohexanetricarboxylic acid were dissolved in 50 ml of chloroform. 6 g of thionyl chloride were added and the mixture was stirred for 1 hour at room temperature (25° C.) and concentrated.

3 g of oleylamine dissolved in 50 ml of methylene chloride, and 10 ml of triethylamine were added. The mixture was heated at 50° C. for 2 hours with stirring.

The precipitate was recovered and washed with water, to give 5 g of desired compound.

EXAMPLE 2

The compound used in this example corresponds to formula (I) in which the three groups R are each chosen from hydrogen and the three groups Y are each chosen from a —CO—NHR' group with R' representing a linear hydrocarbon comprising 18 carbon atoms and comprising a double bond (oleyl chain):

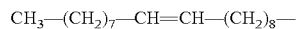

$CH_3—(CH_2)_7—CH=CH—(CH_2)_8—$

A/

50 mg of this compound were mixed with 5 ml of octyldodecanol, with stirring at room temperature, i.e. a mixture comprising 1% of compound (I). The mixture was heated to 107° C. with stirring, until homogenized. It then becomes transparent, homogeneous and fluid. The homogeneous mixture was then left to cool slowly to room temperature.

A transparent, solid, hard composition was thus obtained, which does not collapse when it is outside its container, in the absence of any mechanical or thermal stimulation. This composition can be spread by simple pressure and gives an oily, homogeneous film.

B/

The hardness of the stick obtained was measured using a TA-XT2 texture analyser (from Rheo), at 22° C., using a smooth acrylic cone with an apex angle of 45° C., and a total height which was greater than the penetration distance. The cone penetrates into the sample to a distance of 5 mm, at a speed of 2 mm/s. It was then kept immobile for 300 s, after which it was removed from the sample at a speed of 2 mm/s. The force exerted by the sample on the measuring body was recorded continuously. The maximum force was detected at the end of the penetration phase. This force value reflects the hardness of the sample.

The following result was obtained: 0.042 N

EXAMPLE 3

Comparative Example

For comparison, a mixture of 5 ml of octyldodecanol and 50 mg of compound corresponding to formula (I) in which the three groups R represent hydrogen and the three groups Y were each chosen from a —CO—NHR' group with R' representing a saturated linear hydrocarbon containing 18 carbon atoms (stearyl group), was prepared according to Example 1.

A hard, solid composition of low translucency was thus obtained.

Moreover, it is noted that it is necessary to heat the mixture up to a temperature of at least 120° C. in order to obtain a homogeneous mixture.

EXAMPLE 4

Transparency Measurements

The transparency or translucency was measured by measuring the transmittance, i.e. the percentage of light transmitted through a given sample, in the wavelength range corresponding to the visible range, i.e. from 400 nm to 800 nm.

This transmittance was measured continuously through a sample of thickened oil, placed in a glass cuvette with an optical path length of 1 cm, by difference with a so-called reference sample containing the same pure oil.

The measuring instrument was a Perkin-Elmer Lambda UV-Vis spectrophotometer.

The composition was heated until it was in the form of a homogeneous fluid, and was poured directly into the measuring cuvette. The cuvette was maintained at room temperature until its contents have cooled. The cuvette was then placed in the machine, the reference cuvette containing pure octyldodecanol also being placed in the machine.

The transmittance was measured between from 400 nm to 800 nm.

The following results were obtained:

composition of Example 2: the transmittance varies in a virtually linear continuous manner, from 89% at 400 nm to 96% at 800 nm (maximum value).

This clearly corresponds to a transparent composition.

control composition of Example 3: the transmittance varies in a virtually linear continuous manner, from 2% at 400 nm to 16% at 800 nm (maximum value).

This clearly corresponds to a composition of very low translucency.

EXAMPLE 5

250 mg of the compound of Example 2 were mixed with 5 ml of isododecane and 25 mg of pigment (iron oxides), with stirring at room temperature. The mixture was heated to 107° C., until homogenized. It becomes transparent, coloured, homogeneous and fluid. The mixture was then left to cool slowly to room temperature.

A solid, coloured composition was thus obtained, in the form of a stick. This composition shows no separation of the pigment over time. It gives an oily, homogeneous film.

EXAMPLE 6

In a manner similar to that of the preceding examples; a composition according to the invention was prepared, comprising:

| | |
|---|---|
| compound of Example 2 | 0.8 g |
| pigments (iron oxides) | 0.5 g |
| isododecane | 16 ml |
| parleam oil | 4 ml |

A solid, hard, coloured stick was obtained.

A coloured film was deposited on a glass plate, using the composition thus prepared. The deposit was left to dry for 20 minutes. The deposit is then dry but remains malleable.

A paper tissue was applied to the deposit and was pressed by hand. No coloured trace was observed on the tissue.

Mechanical rubbing of the tissue on the deposit does not result in any transfer of colour (possible entrainment of material).

The composition thus prepared clearly shows good transfer-resistance properties.

What is claimed is:

1. A compound of formula (I):

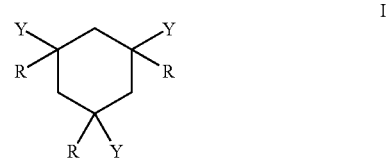

wherein:
R, which may be identical or different, are each chosen from hydrogen atoms and linear and branched, saturated hydrocarbons comprising 1 to 6 carbon atoms;
Y, which may be identical or different, are each chosen from —CO—S—R' groups, —CO—NHR' groups, NH—COR' groups and —S—COR' groups, wherein R', which may be identical or different, are each chosen from
hydrogen atoms,
aryl groups, optionally substituted with at least one hydrocarbon comprising 1 to 22 carbon atoms, wherein said hydrocarbon is chosen from linear and branched, saturated and unsaturated hydrocarbons, and
linear, branched and cyclic, saturated and unsaturated hydrocarbons comprising 1 to 22 carbon atoms;
wherein at least one of said R' groups is chosen from linear and branched, unsaturated hydrocarbons comprising 2 to 22 carbon atoms and one C═C double bond.

2. A compound according to claim 1, wherein R, which may be identical or different, are each chosen from hydrogen atoms and linear and branched, saturated hydrocarbons comprising 1 to 4 carbon atoms.

3. A compound according to claim 1, wherein for R', said linear, branched and cyclic, saturated and unsaturated hydrocarbons comprise 10 to 18 carbon atoms.

4. A compound according to claim 1, wherein at least one of said R' groups is chosen from linear and branched, saturated and unsaturated hydrocarbons comprises 10 to 18 carbon atoms.

5. A compound according to claim 1, wherein at least two of said R' groups are chosen from linear and branched, unsaturated hydrocarbons comprising 2 to 22 carbon atoms and one C═C double bond.

6. A compound according to claim 1, wherein at least three of said R' groups are chosen from linear and branched, unsaturated hydrocarbons comprising 2 to 22 carbon atoms and one C═C double bond.

7. A compound according to claim 1, wherein said R' is chosen from linear and branched hydrocarbons comprising 2 to 22 carbons and one C═C double bond.

8. A compound according to claim 1, wherein said R' is chosen from linear and branched hydrocarbons comprising 10 to 18 carbons and one C=C double bond.

9. A compound according to claim 1, wherein said R' is chosen from caproleyl groups, lauroleyl groups, myristoleyl groups, palmitoleyl groups, oleyl groups, gadoleyl groups, linoleyl groups, linolenyl groups and elaidyl groups.

10. A compound according to claim 1 chosen from:
cis-1,3,5-tris(oleylaminocarbonyl)cyclohexane,
cis-1,3,5-tris(gadoleylaminocarbonyl)cyclohexane,
cis-1,3,5-tris(elaidylaminocarbonyl)cyclohexane,
cis-1,3-bis(oleylaminocarbonyl)-cis-5-(octadecylaminocarbonyl)cyclohexane,
cis-1,3-bis(oleylaminocarbonyl)-cis-5-(dodecylaminocarbonyl)cyclohexane,
cis-1,3-bis(oleylaminocarbonyl)-cis-5-[N-(3,7-dimethyloctyl)aminocarbonyl]cyclohexane,
cis-1-(oleylaminocarbonyl)-cis-3,5-bis(octadecylaminocarbonyl)cyclohexane,
cis-1-(oleylaminocarbonyl)-cis-3,5-bis(dodecylaminocarbonyl)cyclohexane,
cis-1-(oleylaminocarbonyl)-cis-3,5-bis[N-(3,7-dimethyloctyl)aminocarbonyl]cyclohexane,
trans-1,3,5-trimethyl-1,3,5-tris(oleylaminocarbonyl)cyclohexane and
trans-1,3,5-trimethyl-1,3,5-tris(gadoleylaminocarbonyl)cyclohexane.

11. A composition comprising at least one compound of formula (I):

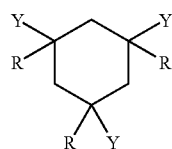

wherein:
R, which may be identical or different, are each chosen from hydrogen atoms and linear and branched, saturated hydrocarbons comprising 1 to 6 carbon atoms;
Y, which may be identical or different, are each chosen from —CO—S—R' groups, —CO—NHR' groups, NH—COR' groups and —S—COR' groups, wherein R', which may be identical or different, are each chosen from
hydrogen atoms,
aryl groups substituted with at least one hydrocarbon comprising 10 to 18 carbon atoms, wherein said hydrocarbon is chosen from linear and branched, saturated and unsaturated hydrocarbons, optionally substituted with at least one hydrocarbon comprising 1 to 22 carbon atoms, wherein said hydrocarbon is chosen from linear and branched, saturated and unsaturated hydrocarbons, and
linear, branched and cyclic, saturated and unsaturated hydrocarbons comprising 1 to 22 carbon atoms;
wherein at least one of said R' groups is chosen from linear and branched, unsaturated hydrocarbons comprising 2 to 22 carbon atoms and one C=C double bond.

12. A composition according to claim 11, wherein R, which may be identical or different, are each chosen from hydrogen atoms and linear and branched, saturated hydrocarbons comprising 1 to 4 carbon atoms.

13. A composition according to claim 11, wherein for R', said linear branched, and cyclic, saturated and unsaturated hydrocarbons comprise 10 to 18 carbon atoms.

14. A composition according to claim 11, wherein at least one of said R' groups chosen from linear and branched, saturated and unsaturated hydrocarbons comprises 10 to 18 carbon atoms.

15. A composition according to claim 11, wherein at least two of said R' groups are chosen from linear and branched, unsaturated hydrocarbons comprising 2 to 22 carbon atoms and one C=C double bond.

16. A composition according to claim 11, wherein at least three of said R' groups are chosen from linear and branched, unsaturated hydrocarbons comprising 2 to 22 carbon atoms and one C=C double bond.

17. A composition according to claim 11, wherein said R' is chosen from linear and branched hydrocarbons comprising 2 to 22 carbons and one C=C double bond.

18. A composition according to claim 11, wherein said R' is chosen from linear and branched hydrocarbons comprising 10 to 18 carbons and one C=C double bond.

19. A composition according to claim 11, wherein said R' is chosen from caproleyl groups, lauroleyl groups, myristoleyl groups, palmitoleyl groups, oleyl groups, gadoleyl groups, linoleyl groups, linolenyl groups and elaidyl groups.

20. A composition according to claim 11, wherein said at least one compound of formula (I) is chosen from:
cis-1,3,5-tris(oleylaminocarbonyl)cyclohexane,
cis-1,3,5-tris(gadoleylaminocarbonyl)cyclohexane,
cis-1,3,5-tris(elaidylaminocarbonyl)cyclohexane,
cis-1,3-bis(oleylaminocarbonyl)-cis-5-(octadecylaminocarbonyl)cyclohexane,
cis-1,3-bis(oleylaminocarbonyl)-cis-5-(dodecylaminocarbonyl)cyclohexane,
cis-1,3-bis(oleylaminocarbonyl)-cis-5-[N-(3,7-dimethyloctyl)aminocarbonyl]cyclohexane,
cis-1-(oleylaminocarbonyl)-cis-3,5-bis(octadecylaminocarbonyl)cyclohexane,
cis-1-(oleylaminocarbonyl)-cis-3,5-bis(dodecylaminocarbonyl)cyclohexane,
cis-1-(oleylaminocarbonyl)-cis-3,5-bis[N-(3,7-dimethyloctyl)aminocarbonyl]cyclohexane,
trans-1,3,5-trimethyl-1,3,5-tris(oleylaminocarbonyl)cyclohexane and
trans-1,3,5-trimethyl-1,3,5-tris(gadoleylaminocarbonyl)cyclohexane.

21. A composition according to claim 11, wherein said at least one compound of formula (I) is present in an amount ranging from 1% to 40% by weight.

22. A composition according to claim 21, wherein said at least one compound of formula (I) is present in an amount ranging from 2% to 10% by weight.

23. A composition according to claim 22, wherein said at least one compound of formula (I) is present in an amount ranging from 3% to 8% by weight.

24. A composition according to claim 23, wherein said at least one compound of formula (I) is present in an amount ranging from 4% to 6% by weight.

25. A composition according to claim 11, further comprising at least one oil chosen from cosmetically acceptable oils and dermatologically acceptable oils.

26. A composition according to claim 11, further comprising at least one oil chosen from hydrocarbon-based oils, silicone oils and fluoro oils.

27. A composition according to claim 26, wherein said at least one oil is volatile.

28. A composition according to claim 26, wherein said at least one oil originates from an origin chosen from animal origins, plant origins, mineral origins and synthetic origins.

29. A composition according to claim 11, further comprising at least one wax in a concentration of less than about 5% by weight relative to the total weight of said composition.

30. A composition according to claim 29, wherein said at least one wax is present in a concentration of less than 2% by weight relative to the total weight of said composition.

31. A composition according to claim 30, wherein said at least one wax is present in a concentration of less than 0.5% by weight relative to the total weight of said composition.

32. A composition according to claim 31, wherein no wax is present in said composition.

33. A composition according to claim 11, wherein said composition is in the form of a solid.

34. A composition according to claim 11, wherein said composition has a hardness ranging from 0.04 N to 3 N.

35. A composition according to claim 34, wherein said hardness ranges from 0.1 N to 2.5 N.

36. A composition according to claim 35, wherein said hardness ranges from 0.5 N to 2 N.

37. A composition according to claim 11, wherein said composition is translucent.

38. A composition according to claim 11, wherein said composition is transparent.

39. A composition according to claim 11, wherein said composition has a maximum light transmittance value, irrespective of its wavelength, ranging from 400 nm and 800 nm, through a 1 cm thick sample, of at least 2%.

40. A composition according to claim 11 in the form chosen from: solid and soft oily gels, optionally comprising water, solid and gelled oil-in-water emulsions, water-in-oil emulsions and multiple emulsions, dispersions of oil in water; multi-phase systems; creams, salves, soft pastes, ointments, cast solids, moulded solids; and transparent anhydrous rigid gels and translucent anhydrous rigid gels.

41. A composition according to claim 40, wherein said multi-phase systems are two-phase systems.

42. A composition according to claim 40, wherein said cast solids are sticks.

43. A composition according to claim 40, wherein said moulded solids are sticks.

44. A composition according to claim 40, wherein said rigid gels are sticks.

45. A compound of formula (I):

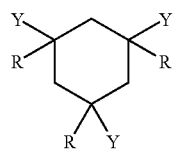

wherein:

R, which may be identical or different, are each chosen from hydrogen atoms and linear and branched, saturated hydrocarbons comprising 1 to 6 carbon atoms;

Y, which may be identical or different, are each chosen from —CO—S—R' groups, —CO—NHR' groups, NH—COR' groups and —S—COR' groups, wherein R', which may be identical or different, are each chosen from hydrogen atoms, aryl groups, optionally substituted with at least one hydrocarbon comprising 1 to 22 carbon atoms, wherein said hydrocarbon is chosen from linear and branched, saturated and unsaturated hydrocarbons, and linear, branched and cyclic, saturated and unsaturated hydrocarbons comprising 1 to 22 carbon atoms;

wherein at least one of said R' groups is chosen from aryl groups, substituted with at least one hydrocarbon comprising 10 to 22 carbon atoms, wherein said hydrocarbon is chosen from linear and branched, unsaturated hydrocarbons.

46. A composition comprising at least one compound of formula (I):

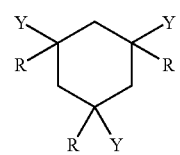

wherein:

R, which may be identical or different, are each chosen from hydrogen atoms and linear and branched, saturated hydrocarbons comprising 1 to 6 carbon atoms;

Y, which may be identical or different, are each chosen from —CO—S—R' groups, —CO—NHR' groups, NH—COR' groups and —S—COR' groups, wherein R', which may be identical or different, are each chosen from hydrogen atoms, aryl groups, optionally substituted with at least one hydrocarbon comprising 1 to 22 carbon atoms, wherein said hydrocarbon is chosen from linear and branched, saturated and unsaturated hydrocarbons, and linear, branched and cyclic, saturated and unsaturated hydrocarbons comprising 1 to 22 carbon atoms;

wherein at least one of said R' groups is chosen from aryl groups, substituted with at least one hydrocarbon comprising 10 to 22 carbon atoms, wherein said hydrocarbon is chosen from linear and branched, saturated and unsaturated hydrocarbons.

* * * * *